(12) United States Patent
Erlich

(10) Patent No.: US 11,456,759 B2
(45) Date of Patent: Sep. 27, 2022

(54) OPTIMIZED ENCODING FOR STORAGE OF DATA ON POLYMERS IN ASYNCHRONOUS SYNTHESIS

(71) Applicant: Erlich Lab LLC, Ra'anana (IL)

(72) Inventor: Yaniv Erlich, Las Vegas, NV (US)

(73) Assignee: Erlich Lab LLC, Ra'ananna (IL)

( * ) Notice: Subject to any disclaimer, the term of this patent is extended or adjusted under 35 U.S.C. 154(b) by 796 days.

(21) Appl. No.: 16/422,121

(22) Filed: May 24, 2019

(65) Prior Publication Data

US 2019/0363739 A1   Nov. 28, 2019

Related U.S. Application Data

(60) Provisional application No. 62/676,757, filed on May 25, 2018.

(51) Int. Cl.

| | |
|---|---|
| *H03M 13/00* | (2006.01) |
| *G16C 20/64* | (2019.01) |
| *G16C 20/10* | (2019.01) |
| *H03M 13/15* | (2006.01) |
| *H03M 13/37* | (2006.01) |
| *H03M 13/29* | (2006.01) |

(52) U.S. Cl.
CPC .......... *H03M 13/611* (2013.01); *G16C 20/10* (2019.02); *G16C 20/64* (2019.02); *H03M 13/154* (2013.01); *H03M 13/1515* (2013.01); *H03M 13/3761* (2013.01); *H03M 13/2906* (2013.01)

(58) Field of Classification Search
CPC ... G06N 3/12; G11C 13/0016; G11C 13/0019
See application file for complete search history.

(56) References Cited

U.S. PATENT DOCUMENTS

| | | | | |
|---|---|---|---|---|
| 11,177,019 | B2 * | 11/2021 | Dai ......................... | G06N 3/12 |
| 2010/0199155 | A1 * | 8/2010 | Kermani ........... | H03M 13/1515 |
| | | | | 714/752 |
| 2018/0253563 | A1 * | 9/2018 | Peck ..................... | H04L 9/3231 |

* cited by examiner

*Primary Examiner* — Lam S Nguyen

(74) *Attorney, Agent, or Firm* — Erik A. Huestis; Foley Hoag LLP

(57) ABSTRACT

Methods for data storage on polymers are provided. In various embodiments, an erasure error correcting code is selected. Input data is read from an input file. The erasure error correcting code is applied to the input data to generate a code word. The code word is encoded according to a chemical alphabet. A number of cycles required for synthesis is determined for the code word. The encoded code word is screened according to the number of cycles. The code word is retained where passing the screening.

20 Claims, 4 Drawing Sheets

OPTIMIZED ENCODING FOR STORAGE OF DATA ON POLYMERS IN ASYNCHRONOUS SYNTHESIS

CROSS-REFERENCE TO RELATED APPLICATIONS

This application claims the benefit of U.S. Provisional Application No. 62/676,757, filed on May 25, 2018, which is hereby incorporated by reference in its entirety.

BACKGROUND

Embodiments of the present disclosure relate to data storage on polymers, and more specifically, to optimized encoding for storage of data on polymers in asynchronous synthesis.

BRIEF SUMMARY

According to embodiments of the present disclosure, methods of and computer program products for optimizing encoding of data for storage on polymers are provided. In various embodiments, an erasure error correcting code is selected. Input data is read from an input file. The erasure error correcting code is applied to the input data to generate a code word. The code word is encoded according to a mapping to a chemical alphabet. A number of cycles required for synthesis is determined for the code word. The encoded code word is screened according to the number of cycles. The code word is retained where passing the screening.

DETAILED DESCRIPTION

Figure 1:
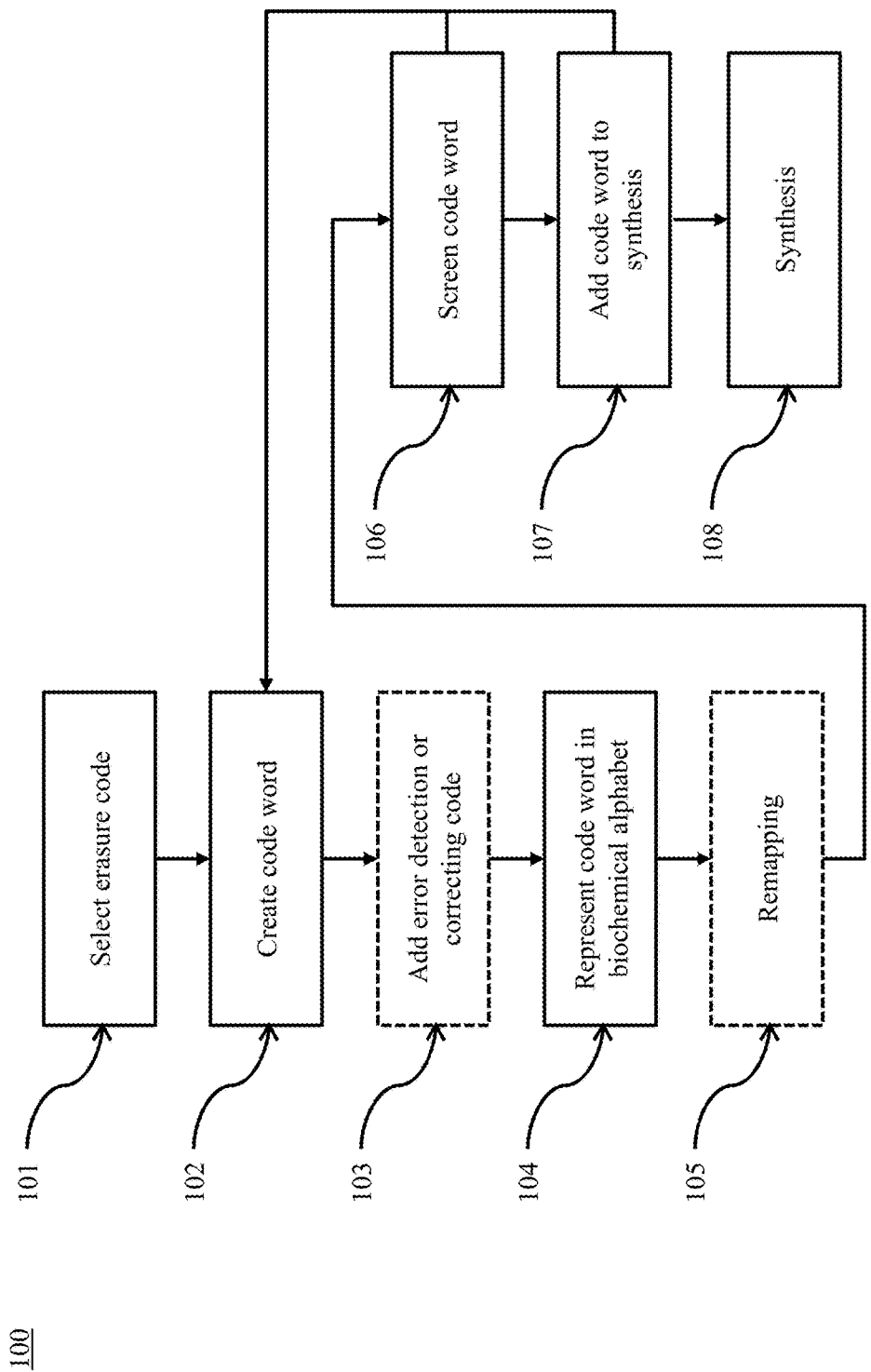
FIG. 1 illustrates a method for data storage on polymers is illustrated according to embodiments of the present disclosure.

Storage using chemical polymers such as DNA offers multiple advantages over conventional digital storage, such as extreme volumetric density, unlimited copies, and an increased life span. Various strategies for storage using polymers may utilize ink jet printers as DNA oligo pool synthesis technology due to their commercial availability for other synthetic biology applications.

Such ink jet technology uses an acid wash step to deprotect all of the features (such as DNA oligos) on the array. The printer head then moves from one feature to another and fires/deposits one of the monomers to the spot according to the design file. This process creates strands that are all synchronized in their synthesis. For example, in the case of DNA, if each oligo is of length of 200 nt, the process takes exactly 200 cycles regardless of the DNA sequence of each oligo. Strategies in which all oligos have the same length at each cycle may be referred to as synchronous synthesis strategies.

Other alternatives for polymer synthesis are available, such as electro-chemical synthesis using silicon electrodes and maskless photolithography. While these two technologies have quite distinct chemical reactions, they create polymer strands in an asynchronous manner. Unlike the ink-jet technology, these technologies deprotect only a subset of the polymer features in each cycle and wash the entire flow-cell with a monomer (e.g., Adenine), which is incorporated to the deprotected sites. In the next cycle, another subset is deprotected and the entire flow-cell is washed with another nucleotide (e.g., Cytosine). This process is repeated in a cyclic manner over the types of monomers until all oligos are synthesized. This approach creates features that will lag behind and will require more synthesis cycles while other features already finished their synthesis. For example, in the case of DNA, if the washes iterate over A→C→G→T→A→ . . . , the sequence ACGT will be finished by the 4th cycle, whereas the sequence AAAA will be finished only by the 13th cycle. Strategies in which oligos may have different lengths at each cycle may be referred to as asynchronous synthesis strategies.

In asynchronous synthesis strategies, the last oligo in the pool to be synthesized determines the overall synthesis time. For example, if the two oligos above (ACGT and AAAA) are synthesized in the same pool, it will take 13 cycles to synthesize the pool despite the fact that the synthesizer does not add any nucleotides to the ACGT oligo in cycles 5 to 13. If the pool has 1 million oligos that take 100 cycles and 1 oligo that takes 400 cycles, the synthesizer will keep working extra 300 cycles to finish the last oligo, reducing the throughput of the machine and wasting reagents and time.

The asynchronous synthesis issue is deeply rooted in the size of the chemical alphabet. In conventional DNA synthesizers, the alphabet consists of four nucleotides. However, DNA storage, and more generally, polymer-based storage, can use other alphabet sets to synthesize oligos. For example, semi-synthetic DNA of an alphabet of six nucleotides may be produced. A further expended DNA alphabet of 16 nucleotides may be utilized by per-marking di-nucleotides as the basic monomer for synthesis. If an architecture relies on amino-acids, the basic alphabet may consist of 20 monomers.

Various encoding algorithms may be adopted to reduce the probability of an error in synthesis or sequencing while maximizing the information content per monomer in synchronous synthesis.

The present disclosure provides a general encoding method that provides robustness for errors and maximizes the information content in asynchronous synthesis. The methods provided herein are general and minimize the number of cycles to synthesize a pool with n oligos with a general chemical alphabet of k letters.

Referring to FIG. 1, a method for data storage on polymers is illustrated according to embodiments of the present disclosure. As noted above, the oligo with the maximal number of cycles determines the overall required number of cycles. The encoding techniques described herein minimize the maximal number of cycles with a minimal reduction in the information content.

At 101, an erasure error correcting code is selected. Exemplary codes include DNA Fountain or Reed-Solomon code, although it will be appreciated that additional error correcting codes may be used according to the present disclosure. At 102, the error correcting code is used to create a code word from an input file. In some embodiments, an error detection or error correcting code is added at 103 to create robustness to errors in the oligo. It will be appreciated that a variety of error detection and correcting codes are known in the art, for example, parity, Hamming, and CRC. At 104, the code word is represented using the biochemical alphabet. In some embodiments, a representation is also selected that could have a smaller number of cycles by a remapping step 105. At 106, the code word is computationally screened for (i) the number of cycles it would take to be synthesized and optionally for (ii) undesired biochemical properties. At 107, if the code word passes the screen, it is added to the oligos to be synthesized. Step 102 . . . 107 are repeated at least until there are a sufficient number of oligos based on information theoretic requirements of the error correcting code.

The process described above sets a maximal number of cycles that is user controlled, creates robustness to errors, and has a minimal effect on the information content.

Let k be the chemical alphabet of the synthesizer, n the number of oligos, and l the desired length of the oligo pool. Let the digits $\{0, \ldots, k-1\}$ represent the symbols of the chemical alphabet and let $s=s_1 s_2 s_3 \ldots s_l$ denotes an oligo sequence. For example, in the case of DNA, 0 may denote A, 1 may denote C, 2 may denote G, and 3 may denote T. In this exemplary encoding, the sequence ACGTGC is represented as 012321. Next, let $q=\{s_1, s_2, \ldots\}$ be the order in which the monomer is applied to the synthesizer in a modular fashion and let |q| be the number of elements in q. For example, in DNA sequencing that rotates between $\{A,C,G,T\}$, $q=\{0,1,2,3\}$ and $|q|=4$. In the i-th cycle (with 0-based numbering), the machine applies the monomer that corresponds to i modulo |q| monomer. For example, with $q=\{0,1,2,3\}$, in the $0^{th}$ cycle, the machine applies "A" according to 0 mod 4=0; in the $1^{st}$ cycle, the machine applies "C" according to 1 mod 4=1; and in the $4^{th}$ cycle, the machine applies "A" again according to 4 mod 4=0. Generally, q can be very long such as "$\{0,0,0,0,1,2,3,4,1,2,3,4,1,2,3,4\}$". In the special case, where q just rotates over the alphabet without repeating any letter, it is referred to as standard q and given below as $q_k$. For example, $q_4$ refers to $q=\{0,1,2,3\}$.

Let w(s; q) denotes a function that returns the number of cycles required to synthesize the sequence s using the cycle q. For example, $w(0123; q_4)=4$ and $w(0000; q_4)=13$. Herein w(s, q) is referred to as the weight of the sequence s under q. For a standard q, the weight is given by Equation 1 where $\Delta(a, b)$ is defined in Equation 2.

$$w(s, q) = s_1 + \sum_{i=1}^{l-1} \Delta(s_{i+1} - s_i) \quad \text{Equation 1}$$

$$\Delta(a, b) = \begin{cases} b-a \mod k; & \text{if } a \neq b \\ k, & \text{otherwise} \end{cases} \quad \text{Equation 2}$$

The number of cycles needed to synthesize the n oligos is determined by the oligo with the highest weight.

$$L = \max w(x,q), x \in x_1, x_2, \ldots, x_n \quad \text{Equation 3}$$

In alternative encoding strategies, the maximal cycles can be approximated by Dodd's (1923) extreme value of a Gaussian.

$$\mathbb{E}[L] \approx \frac{(k+1)l}{2} + \sqrt{\frac{(k^2-1)l}{6} \log_e n} \quad \text{Equation 4}$$

Figure 2:
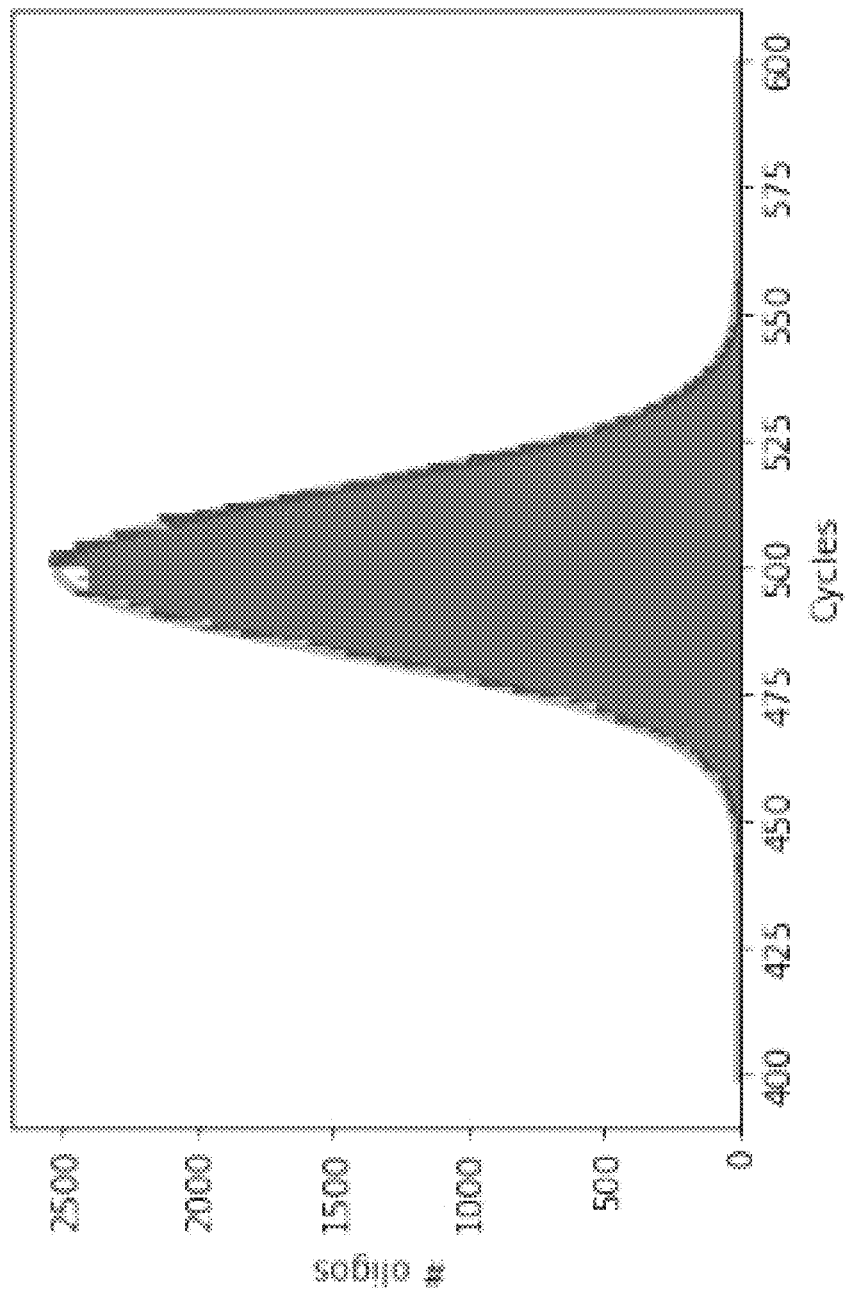
FIG. 2 illustrates a weight distribution for a method according to embodiments of the present disclosure.

Referring to FIG. 2, a weight distribution is illustrated for a simulation of n=100,000 oligos of length 2 using $q_4$ synthesis. The empirical weight distribution is presented (area) vs. the Gaussian approximation (curve). The maximal observed weight, L, was 576 and the expected maximal weight, E[L], based on the equation above is 570. It can be seen that some oligos are finished to synthesized after 450 cycles and most oligos finished to be synthesized by 500 cycles the extra cycles to get to 576 are only required for very few oligos.

Referring back to FIG. 1, Algorithms according to embodiments of the present disclosure proceed as follows. An erasure error correcting code is selected (101). In various embodiments, the erasure code may be DNA Fountain or Reed-Solomon code. A user specifies the maximal number of cycles (denoted as LL) either as an absolute number (e.g., LL=475) or as a p value (e.g., p=0.01). If the latter, LL is computed from the p value using the following equations.

$$m = \frac{l(k+1)}{2} \quad \text{Equation 5}$$

$$v = \frac{l(k^2-1)}{12} \quad \text{Equation 6}$$

$$LL = np. \quad \text{Equation 7}$$
$$round(scipy.stats.norm.ppf(p, loc = m, \text{scale} = np.sqrt(v)))$$

In Equation 7, scipy.stats.norm.ppf denotes a function that returns the value of the inverse of a normal cumulative function for p with a mean denoted by the loc parameter and standard deviation denoted by the scale parameters. np.sqrt (x) denotes algebraic root of x, and np.round(x) is a function that rounds x to its closest integer.

If the algorithm uses a (K, N)-Reed-Solomon code, the algorithm picks an N that is bigger than p*K.

A single code word is generated from an input file using the normal functions of the erasure error correcting code (102). Optionally, an error correcting code or an error detecting code is added to the oligo before or after 102.

The oligo is mapped into the k-mer alphabet (104). In some embodiments, direct mapping is employed. In direct mapping, a letter from the alphabet is assigned for each binary sequence. For example, in the case of $q_4$, the algorithm can map 00 to A, 01 to C, 10 to G, and 11 to T.

In some embodiments, remapping is employed (105). Remapping starts with the direct mapping above. Next, it inspects the $\Delta(a, b)$ function above on pairs of nucleotides and write the sequence of results. Then, it appends the value of first monomer. This sequence consists of l numbers with possible values between 1 and some other integer that represent the number of cycles between each possible letters. Next, the algorithm counts the value of each type and creates a histogram.

For example, consider the case of $q_4$ and the sequence ACCTTG. The result of $\Delta(a, b)$ will be $\Delta(A, C)=1$, $\Delta(C, C)=4$, $\Delta(C, T)=2$, $\Delta(T, T)=4$, $\Delta(T, G)=3$ and the sequence is 1,4,2,4,3. The algorithm then appends the value of A to the left to get the sequence 1,1,4,2,4,3. Finally, the algorithm creates a histogram. 1 appears 2 times, 2 appears 1 time, 3 appears 1 time, and 4 appears 2 times.

Next, the algorithm remaps the symbols based on the values of the histogram. It starts by remapping the symbol with the highest count to 1, then it remaps the symbol with the second highest count to 2, and so on until all k symbols are mapped and produces the remapped sequence. In the example above, 1 and 4 are the two symbols with highest counts because they appear twice and then 2 and 3 appears only once. Thus, the algorithm will remap 1→1 and 4→2 and 3→3 and 2→4. The output sequence will be 1,1,2,4,2,3.

There are k! possible methods to remap any histogram with k symbols. After remapping, the algorithm examines which one of the k! methods was selected. The algorithm assigns a unique number for each of these possible remapping techniques and appends the number to the end. For example, in the case of $q_4$, remapping #0 can denote 1→1, 2→2, 3→3, 4→4, remapping #1 can denote 1→2, 2→1, 3→3, 4→4, and say that remapping #19 1→1, 2→4, 3→3, 4→2. In our example above, where 1,1,4,2,4,3 was remapped to 1,1,2,4,2,3, the algorithm used remapping #19. The algorithm stores the remapping number used for the oligo. Next, the algorithm converts the output into a sequence by picking an element from q in a cyclic manner. In our example with q={A,C,G,T}, the remapped sequence 1,1,2,4,2,3 starts with 1. This 1 corresponds to the first position in q, which is A; then, the next 1 (1,1,2,4,2,3) corresponds to C because C is 1 position after A in q; then, 2 (1,1,24,2,3) corresponds to T because T is 2 positions after C, then 4 (1,1,2,4,2,3) corresponds to T again, because walking 4 positions in q in a cyclic manner yields another T; The next 2 (1,1,2,4,2,3) corresponds to C, and 3 (1,1,2,4,2,3) corresponds to A. The output sequence is then AATTCA. Finally, the algorithm appends to the right the remapping number in a regular DNA format. For example, in our case, the remapping number was 19, which corresponds to 010011 and to 01→G, 00→A, 11→T. Thus, the remapping number corresponds to the prefix GAT, which is appended to the oligo to get AATTCAGAT.

It will be appreciated that in various embodiments, any other dictionary may be used that maps binary words into another alphabet or a word from an alphabet. For example, in the case of $q_4$, 000000 can be mapped to ACG and 00001 to CCG and so on. The permitted words (e.g., "ACG") can be selected to be below a certain weight, where weight is denoted by w and defined by Equation 8 below.

The algorithm computationally screens (106) the oligo from the previous stage for the number of cycles it would take to be synthesized by applying Equation 8. If w(s,q)<LL, then the algorithm goes to the next step.

$$w(s, q) = s_1 + \sum_{i=1}^{l-1} \Delta(s_{i+1} - s_i) \qquad \text{Equation 8}$$

Optionally, the algorithm also screens for undesired biochemical properties such as homopolymer runs or secondary structures. Examples of such approaches are described in *DNA Fountain enables a robust and efficient storage architecture*, Science. 355 (6328): 950-954. doi:10.1126/science.aaj2038, which is hereby incorporated by reference in its entirety.

If the oligo passes the screen or screens, it is added (107) to the oligos to be synthesized. If not, it is discarded.

The above steps are repeated at least until there is a sufficient number of oligos based on information theoretic requirements of the error correcting code.

Figure 3:
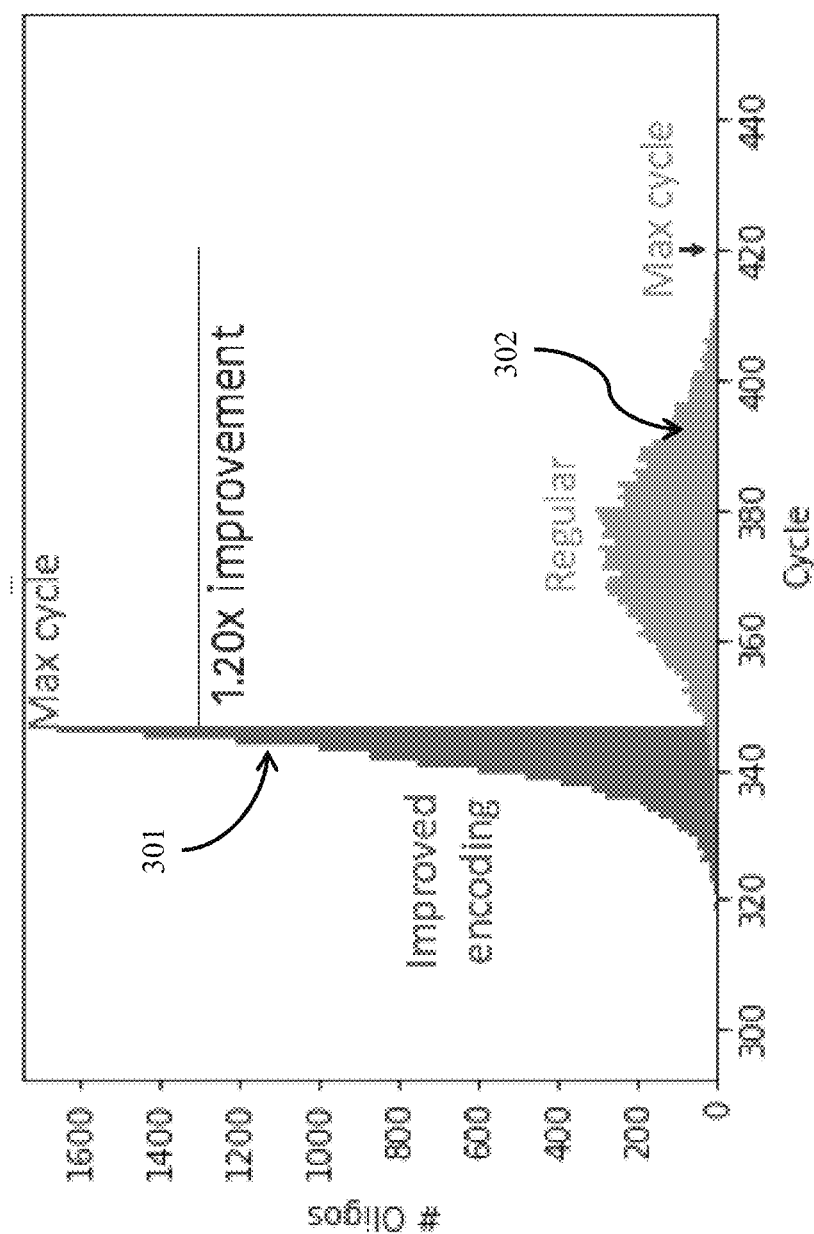
FIG. 3 is a histogram illustrating the performance of methods according to the present disclosure.

FIG. 3 is a histogram showing the performance of the above algorithm with p=0.02 for 150 nt and 10,000 simulated oligos versus the same oligos using a regular encoding strategy. In the regular coding strategy, 420 cycles are required to synthesize the oligos. With the above algorithm, only 346 cycles are required to synthesize.

Figure 4:
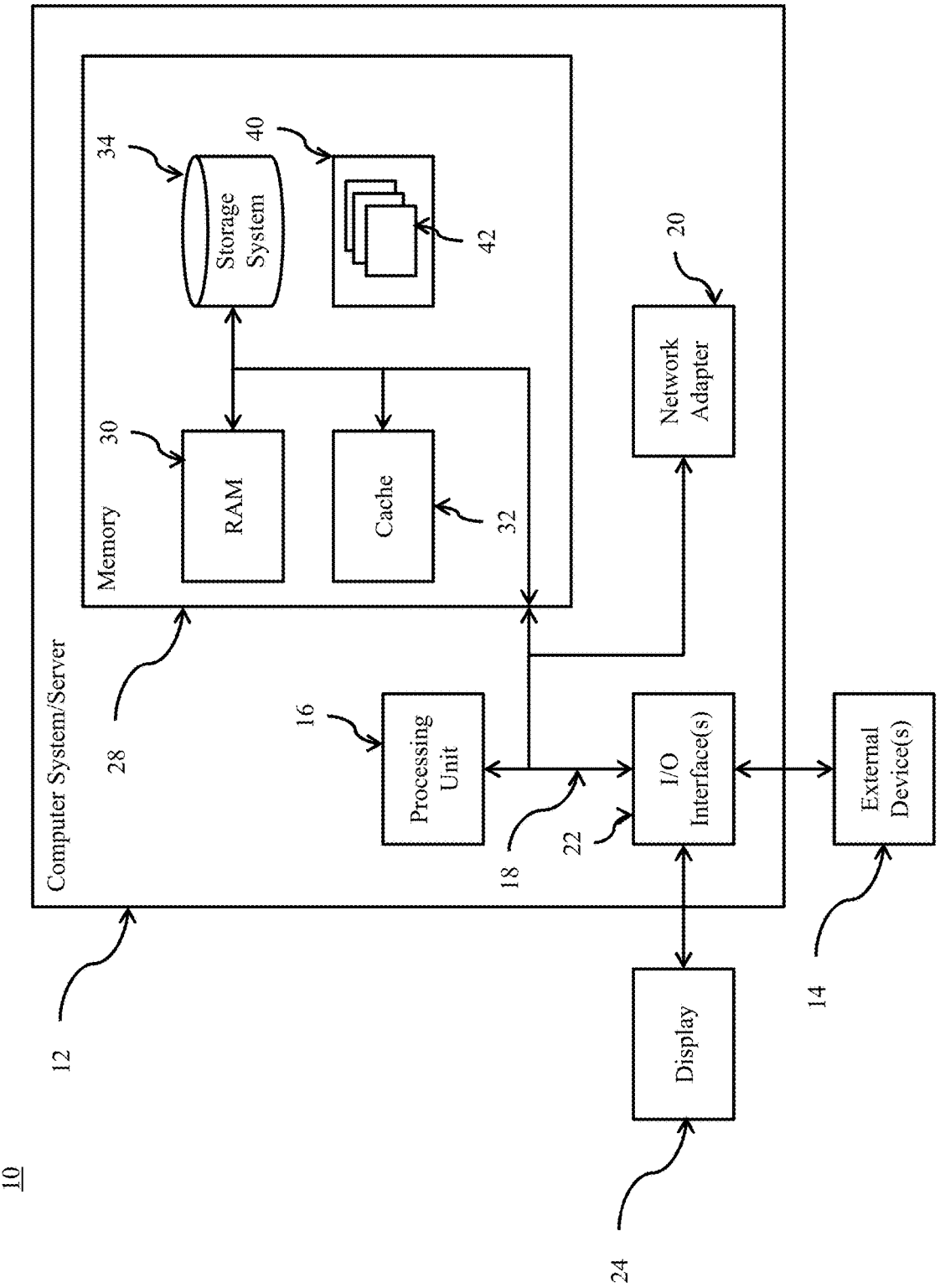
FIG. 4 depicts a computing node according to an embodiment of the present disclosure.

Referring now to FIG. 4, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, graphical processing units (GPUs), and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   selecting an erasure error correcting code;
   reading input data from an input file;
   applying the erasure error correcting code to the input data to generate a code word;
   encoding the code word according to a chemical alphabet;
   determining for the code word a number of cycles required for synthesis;
   screening the encoded code word according to the number of cycles;
   retaining the code word where passing the screening.

2. The method of claim 1, further comprising:
   repeating said applying, encoding, and screening until a predetermined number of code words is retained.

3. The method of claim 1, further comprising:
   screening the encoded code word for undesired chemical properties.

4. The method of claim 1, further comprising:
   synthesizing the code word on a polymer.

5. The method of claim 1, wherein the erasure error correcting code comprises DNA Fountain or Reed-Solomon code.

6. The method of claim 1, further comprising:
   adding an error detecting or error correcting code to the code word.

7. The method of claim 1, wherein encoding the code word comprises mapping each of a plurality of binary sequences of the code word to a letter in the chemical alphabet.

8. The method of claim 7, wherein said mapping further comprises looking up each of the plurality of binary sequences in a table, the table mapping binary substrings to code words whose each individual weight are below a predetermined threshold.

9. A system comprising:
   a computing node comprising a computer readable storage medium having program instructions embodied therewith, the program instructions executable by a processor of the computing node to cause the processor to perform a method comprising:
   selecting an erasure error correcting code;
   reading input data from an input file;
   applying the erasure error correcting code to the input data to generate a code word;
   encoding the code word according to a chemical alphabet;
   determining for the code word a number of cycles required for synthesis;
   screening the encoded code word according to the number of cycles;
   retaining the code word where passing the screening.

10. The system of claim 9, the method further comprising:
    repeating said applying, encoding, and screening until a predetermined number of code words is retained.

11. The system of claim 9, the method further comprising:
    screening the encoded code word for undesired biochemical properties.

12. The system of claim 9, the method further comprising:
    synthesizing the code word.

13. The system of claim 9, wherein the erasure error correcting code comprises DNA Fountain or Reed-Solomon code.

14. The system of claim 9, the method further comprising:
    adding an error detecting or error correcting code to the code word.

15. A computer program product for data storage on polymers, the computer program product comprising a computer readable storage medium having program instructions embodied therewith, the program instructions executable by a processor to cause the processor to perform a method comprising:
    selecting an erasure error correcting code;
    reading input data from an input file;
    applying the erasure error correcting code to the input data to generate a code word;
    encoding the code word according to a chemical alphabet;
    determining for the code word a number of cycles required for synthesis;
    screening the encoded code word according to the number of cycles;
    retaining the code word where passing the screening.

16. The computer program product of claim 15, the method further comprising:

repeating said applying, encoding, and screening until a predetermined number of code words is retained.

17. The computer program product of claim 15, the method further comprising:
screening the encoded code word for undesired biochemical properties.

18. The computer program product of claim 15, the method further comprising:
synthesizing the code word.

19. The computer program product of claim 15, wherein the erasure error correcting code comprises DNA Fountain or Reed-Solomon code.

20. The computer program product of claim 15, the method further comprising:
adding an error detecting or error correcting code to the code word.

* * * * *